United States Patent [19]

Stec et al.

[11] Patent Number: 6,107,527
[45] Date of Patent: *Aug. 22, 2000

[54] PROCESS FOR THE PRODUCTION OF HYDROXY-AROMATIC SUBSTANCES

[75] Inventors: Zbigniew Stec; Jan Zawadiak, both of Gliwice, Poland; Ulrich Knips, Kamen; Robert Zellerhoff, Hamminkeln, both of Germany; Danuta Gilner, Gliwice, Poland; Beata Orlinska, Katowice, Poland; Jerzy Polaczek, Warsaw, Poland; Witold Tecza, Raszyn, Poland; Zofia Machowska, Warsaw, Poland

[73] Assignee: Rutgers Kureha Solvents GmbH, Duisburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/821,018

[22] Filed: Mar. 19, 1997

[30] Foreign Application Priority Data

Mar. 20, 1996 [PL] Poland ................................... 313419

[51] Int. Cl.$^7$ ................................................. C07C 37/00
[52] U.S. Cl. ......................... 568/741; 568/573; 568/574; 568/575; 568/798
[58] Field of Search ..................... 568/577, 798, 568/802, 573, 575, 741

[56] References Cited

U.S. PATENT DOCUMENTS

| | | | |
|---|---|---|---|
| 2,302,466 | 11/1942 | Palmer | 260/592 |
| 2,628,983 | 2/1953 | Aller | 260/621 |
| 2,628,984 | 2/1953 | Aller | 260/621 |
| 2,751,418 | 6/1956 | Enos, Jr. | 260/610 |
| 3,647,866 | 3/1972 | Ito | 260/524 |
| 3,803,243 | 4/1974 | Brownstein | 260/610 |
| 3,939,211 | 2/1976 | Spector et al. | 260/610 B |
| 4,013,725 | 3/1977 | Yonemitsu | 260/610 |
| 4,288,637 | 9/1981 | Matsunaga | 568/575 |
| 4,929,771 | 5/1990 | Clausen | 568/798 |
| 5,015,786 | 5/1991 | Araki | 568/798 |
| 5,017,729 | 5/1991 | Fukuhara | 568/798 |
| 5,196,598 | 3/1993 | Iwane | 568/575 |

FOREIGN PATENT DOCUMENTS

| | | |
|---|---|---|
| 0308133 | 3/1989 | European Pat. Off. . |
| 0370729 | 5/1990 | European Pat. Off. . |
| 610293 | 3/1947 | United Kingdom . |
| 626095 | 7/1949 | United Kingdom . |
| 641250 | 8/1950 | United Kingdom . |
| 654035 | 5/1951 | United Kingdom . |
| 754862 | 8/1956 | United Kingdom . |
| 757164 | 9/1956 | United Kingdom . |
| 760367 | 10/1956 | United Kingdom . |
| 1284326 | 8/1972 | United Kingdom . |
| 1496227 | 12/1977 | United Kingdom . |

*Primary Examiner*—Michael L. Shippen
*Attorney, Agent, or Firm*—Hedman, Gibson & Costigan PC

[57] ABSTRACT

The process for the production of hydroxy aromatic substances by means of catalytic oxidation of isoalkyl aromatic substance with oxygen, and decomposition of the hydroperoxide thus formed, is based on the concept that isoalkylaromatic substances are emulsified with an aqueous catalyst solution and brought to a temperature ranging from 50° C. up to the boiling temperature of the emulsion; thereupon the oxygen is allowed to act for 2 to 20 hours and the hydroperoxide formed decomposed, in the presence of an inorganic acid as catalyst, into an hydroxyaromatic substance and a ketone.

8 Claims, No Drawings

PROCESS FOR THE PRODUCTION OF HYDROXY-AROMATIC SUBSTANCES

The invention relates to a process for the production of hydroxyaromatic substances, in particular B-naphthol, cumene, p-cresol and resorcin by catalytic oxidation of isopropylated or isobutylated aromatic substances, and decomposition of the resulting hydroperoxide. A corresponding process is represented in the following reaction equation by way of example, for the production β-naphthol

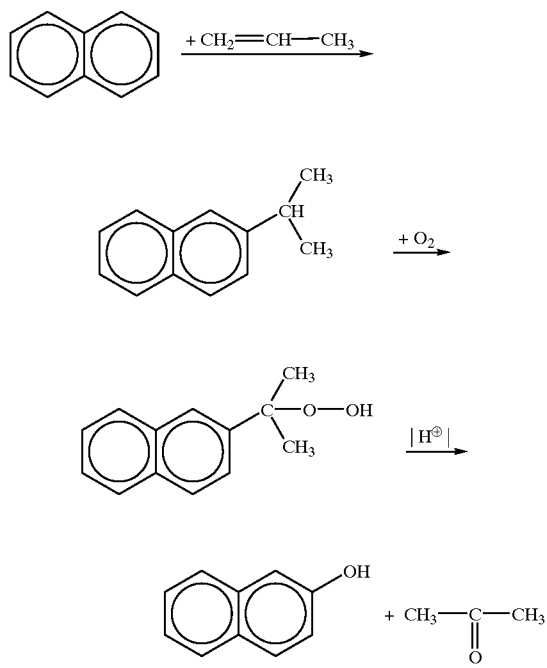

This process, which is described in H. G. Franck, J. W. Stadelhofer, Industrielle Aromatenchemie, Springer publishing house, 1987, cannot be carried out on an industrial scale, however, since in the oxidation of 2-isopropyl naphthalene (2-IPN) only a very low conversion is achieved, so that ultimately the maximally attained hydroperoxide content does not exceed 30%. A further hindrance in performing this process is providing of a technical raw material as starting material which is free from, or contains only little, 1-isopropyl naphthalene. This impairs the conversion of 2-isopropyl naphthalene to the hydroperoxide of the 2-isopropyl naphthalene. If the staring material contains, for example, 10% 1-IPN, the maximal hydroperoxide-2-IPN concentration in the product amounts even to only 20%.

The problem underlying the invention, therefore, is the provision of a process for using process streams containing 1- and 2-isopropylnaphthalene without pre-purification of the same for the production of compounds of the general formula ArOH, such as β-naphthol.

This problem is solved by a process for the production of hydroxyaromatic substances by catalytic oxidation of 2-isoalkyl aromatic substances with oxygen and decomposition of the formed hydroperoxides, in which the starting substance mixture containing the isoalkyl-aromatic substance is agitated with an aqueous catalyst solution up to the formation of an emulsion, warmed to a temperature ranging from 50° C. up to the boiling temperature of the emulsion, exposed for 2 to 20 hours to the action of oxygen, and the resulting hydroperoxide is split in the presence of an inorganic acid into a hydroxyaromatic substance and a ketone.

Isoalkylaromatic substances to be used according to the invention are isopropyl- and isobutyl-aromatic substances which have a tertiary hydrogen in alpha position to the aromatic ring and are represented by the general formula Ar—CHRR' in which R and R' are the same or different and represent methyl, ethyl, and propyl. Ar represents phenyl and its homologues as well as naphthyl and its homologues. Homologues of phenyl are, for example, toluyl, benzyl or xylyl as well as phenyl substituted by one or more methyl or ethyl groups, homologues of naphthyl are the methyl and ethyl derivatives thereof. To be mentioned by way of example are 2-isopropyl naphthalene, p-cymene, m-diisopropyl benzene.

It has proved, surprisingly, that by the process of the invention, for example, a conversion of 2-isopropyl naphthalene to the hydroperoxide of more than 50% is possible in one reaction stage, even if the technical raw material contains 8 to 11% of 1-isopropyl naphthalene. After the disintegration of the hydroperoxide the B-naphthol yield, for example, amounts to 86%.

As catalyst there are used preferably inorganic or organic copper compounds, inorganic cyanides or organic nitriles that activate the oxidation. Especially preferred copper compounds are the chlorides, stearates, acetates, carbonates, acetylacetones, bromides and copper(I)- and copper(II)-oxides. These copper compounds are introduced preferably in an amount of 0.000001 to 0.01 mole per mole of 2-isopropyl naphthalene. The inorganic cyanides and the organic nitriles to be especially preferably introduced are sodium-, potassium- and ammonium-cyanide, acetonitrile, chloroacetonitrile, benzonitrile, azo-bis-cyanocyclohexane, azo-bis-butyronitrile and tetracyanoethylene.

These are preferably used in a quantity ranging from 0.00001 to 0.2 mol per mol of 2-isopropyl naphthalene.

According to an embodiment preferred according to the invention, alkalihydroxides of alkalimetal carbonates can be used in an amount of 0.001 to 1 mass %, with respect to the mass of the catalyst solution. Preferably the hydrocarbon phase stands in a volume ratio of 1:5 to 3:1 to the aqueous catalyst solution; according to an especially preferred form of execution, however, the emulsification occurs in the ratio of 1:1.

After oxidation is completed, the organic phase is separated from the aqueous phase, diluted with acetone, for example 10 to 200 parts by weight of acetone, and the 2-isopropyl naphthalene hydroperoxide contained in it is decomposed by warming to a temperature of 20 to 70° C. in the presence of an inorganic acid, for example sulfuric acid. This reaction is preferably carried out at the boiling temperature of acetone, as the organic phase is introduced into the acetone solution of the inorganic acid. The β-naphthol thus formed can be easily separated out by means of extraction with alkaline solutions or by means of crystallization or distillation, and the hydrocarbon layer after the extraction is additionally oxidized with hydrogen peroxide in the presence of an inorganic acid as catalyst, after which the additionally obtained hydroperoxides are again decomposed.

The production of β-naphthol according to the process of the invention has, in comparison to the already known processes, many advantages. The process procedure according to the invention makes possible in particular a 50 % conversion of the 2-isopropyl naphthalene contained in the starting material to the hydroperoxide in one passage, and by the additional treatment of the mixture after the separating-out of the β-naphthol with hydrogen peroxide, this conversion can be increased in one passage to 60 to 70%.

This process can also be used for the production of phenol from cumene, p-cresol from p-cymene, and resorcin from m-diisopropylbenzene, thus, the products of the process of the invention are within the general formula ArOH, in which Ar has the same meaning as defined before. The following examples explain the invention.

EXAMPLE I

Into a thermostatic glass reactor with a magnetic agitating mechanism, there are introduced 3 g of technical 2-isopropyl naphthalene (Rutgers Kureha Solvents GmbH, Duisburg, Germany), purity 90.2%; 1-isopropyl naphthalene content 9.0%; 3 cm³ of 0.3-percent aqueous NaOH solution, 0.001 g of palmitic acid and 0.0005 g of copper cyanate; all this is mixed for 15 minutes at room temperature to emulsion formation and then warmed to 90° C.

Technical oxygen is then supplied and the emulsion is heated for 13 hours at this temperature. After the separating-off of the aqueous layer by means of a centrifuge, the organic layer contains 54.3% of 2-isopropyl naphthalene hydroperoxide and 9.3% of 2-isopropyl naphthyl alcohol.

This layer is then instilled into boiling one-percent sulfuric acid solution in acetone, with simultaneous separating-off of the acetone that has formed during the decomposition of the hydroperoxide. After the extraction of the distillation residue with 15% sodium hydroxide solution and the saturation of the extract with 20% sulfuric acid solution there is obtained 1.18 g of β-naphthol which, after single recrystallization from diluted ethanol, melts at a temperature of 121.9° C. Into the organic layer there are then added, after the extraction, 3 cm3 of 30% hydrogen peroxide solution and sulfuric acid, whereby there is obtained further 2-isopropyl naphthalene hydroperoxide, which yields after its decomposition (as above) additionally 0.16 g of B-naphthol.

EXAMPLES II TO IX

In the same manner as in example I and with use of the catalysts, activators and process conditions presented in Table 1, there are achieved the conversions, mentioned in Table 1, of the 2-isopropyl naphthalene into the hydroperoxide of technical 2-isopropyl naphthalene, the characteristic of which is to be seen from example I.

In all these cases there are obtained 1.03 to 1.16 g of β-naphthol and in addition about 0.13 to 0.17 g of β-naphthol after decomposition of the hydroperoxide that has arisen during the oxidation of the 2-isopropyl naphthol alcohol with hydrogen peroxide.

TABLE 1

| example | water phase (3 cm³) | catalyst + activator | surfactant | reaction time (h) | reaction-temperature (° C.) | conversion of 2-isopropyl naphthaline to hydroperoxide % |
|---------|---------------------|----------------------|------------|-------------------|-----------------------------|----------------------------------------------------------|
| II | 0.3% NaOH | CuCl₂.2H₂O NaCN | palmitic acid | 12 | 90 | 50.9 |
| III | 0.3% NaOH | copper(II)stearate azobicyclohexylnitrile | — | 12 | 92 | 49.9 |
| IV | 1% NaOH | copper(II)stearate benzonitrile | — | 13 | 92 | 50.3 |
| V | 1% NaOH | copper(II)stearate chloracetonitrile | — | 13 | 92 | 50.1 |
| VI | 1% KOH | CuCl₂.2H₂O KCN | stearinic acid | 12 | 90 | 50.7 |
| VII | 1% KOH | copper(II)nitrate tetracyanoethylene | stearinic acid | 12 | 90 | 50.9 |
| VIII | 1% KOH | Cu₂O azobisisobutyronitrile | palmitic acid | 10 | 92 | 51.3 |
| IX | 1% Na₂CO₃ | copper(II)stearate azobicyclohexylnitrile | palmitic acid | 12 | 90 | 45.0 |

What is claimed is:

1. A process for producing hydroxy naphthalene substances comprising emulsifying an isoalkyl naphthalene in an aqueous catalyst solution comprising a catalyst comprising an inorganic cyanide or organic nitrile; catalytically oxidizing the isoalkyl naphthalene in said emulsion by warming said emulsion to a temperature ranging from 50° C. up to the emulsion boiling temperature and exposing said emulsion to oxygen for two to twenty hours to produce an organic phase comprising a hydroperoxide and an aqueous phase;

separating said organic phase from said aqueous phase; and adding an inorganic acid to said organic phase to decompose said hydroperoxide into said hydroxy isoalkyl naphthalene substance and a ketone.

2. A process according to claim 1 wherein said isoalkyl naphthalene comprises 2-isopropyl-naphthalene and said hydroxy naphthalene substance comprises β-naphthol.

3. A process according to claim 1 wherein the oxidation catalyst comprises a copper cyanide in an amount ranging from about 0.000001 to 0.01 mole per mole of isoalkyl aromatic or an organic nitrile in an amount ranging from 0.00001 to 0.2 moles per mole of isoalkyl naphthalene substance.

4. A process according to claim 1 wherein the oxidation catalyst comprises copper cyanide in an amount ranging from 0.000001 to 0.01 mole per mole of isoalkyl naphthalene.

5. A process according to claim 1 wherein said catalyst solution further comprises alkali hydroxides or alkali carbonates in an amount ranging from 0.0001 to 1 part by weight per 100 parts by weight of said catalyst solution.

6. A process according to claim 1 wherein said catalyst solution further comprises a surface active substance in an amount of 0.0001 to 0.1 part by weight per 100 parts by weight of said catalyst solution.

7. A process according to claim 6 wherein said surface active substance comprises fatty acids or fatty acid salts.

8. A process according to claim 1 wherein said isoalkyl naphthalene is emulsified with an aqueous catalyst solution in a volume ratio of 1:1.

* * * * *